United States Patent
Mathot et al.

(10) Patent No.: US 10,274,405 B2
(45) Date of Patent: Apr. 30, 2019

(54) DEPARAFFINIZATION OF FFPE TISSUE SAMPLES

(71) Applicant: Exscale Biospecimen Solutions AB, Uppsala (SE)

(72) Inventors: Lucy Mathot, Uppsala (SE); Karin Hartman, Uppsala (SE); Tobias Sjöblom, Uppsala (SE)

(73) Assignee: EXSCALE BIOSPECIMEN SOLUTIONS AB, Uppsala (SE)

( * ) Notice: Subject to any disclaimer, the term of this patent is extended or adjusted under 35 U.S.C. 154(b) by 0 days.

(21) Appl. No.: 15/361,116

(22) Filed: Nov. 25, 2016

(65) Prior Publication Data
US 2018/0148713 A1    May 31, 2018

(51) Int. Cl.
*G01N 1/30* (2006.01)
*G01N 1/31* (2006.01)

(52) U.S. Cl.
CPC ............... *G01N 1/31* (2013.01); *G01N 1/30* (2013.01)

(58) Field of Classification Search
None
See application file for complete search history.

(56) References Cited

U.S. PATENT DOCUMENTS

| | | | |
|---|---|---|---|
| 5,344,637 A | 9/1994 | Camiener | |
| 6,632,598 B1 | 10/2003 | Zhang et al. | |
| 8,574,868 B2 | 11/2013 | Lin | |
| 9,845,488 B2 | 12/2017 | Kirsch et al. | |
| 2013/0280787 A1* | 10/2013 | Mueller | C12N 15/1003 435/219 |

OTHER PUBLICATIONS

HISTOCHOICE® Safety Data Sheet dated Mar. 13, 2018.

* cited by examiner

*Primary Examiner* — Joseph G. Dauner
(74) *Attorney, Agent, or Firm* — Porter Wright Morris & Arthur LLP

(57) ABSTRACT

A method for deparaffinizing an FFPE tissue sample comprises mixing the FFPE tissue sample with an organic solvent to form a first mixture (10). A surfactant is added to the first mixture (10) to form a second mixture. The second mixture is separated into an organic solvent layer (11) and a surfactant layer (12). The surfactant layer (12) comprises a deparaffinized tissue sample from the FFPE tissue sample. The method also comprises adding water or an aqueous solution to the separated second mixture to form an organic solvent layer (11), a water or aqueous solution layer (13) and a surfactant layer (12). This surfactant layer comprises the deparaffinized tissue sample.

20 Claims, 6 Drawing Sheets

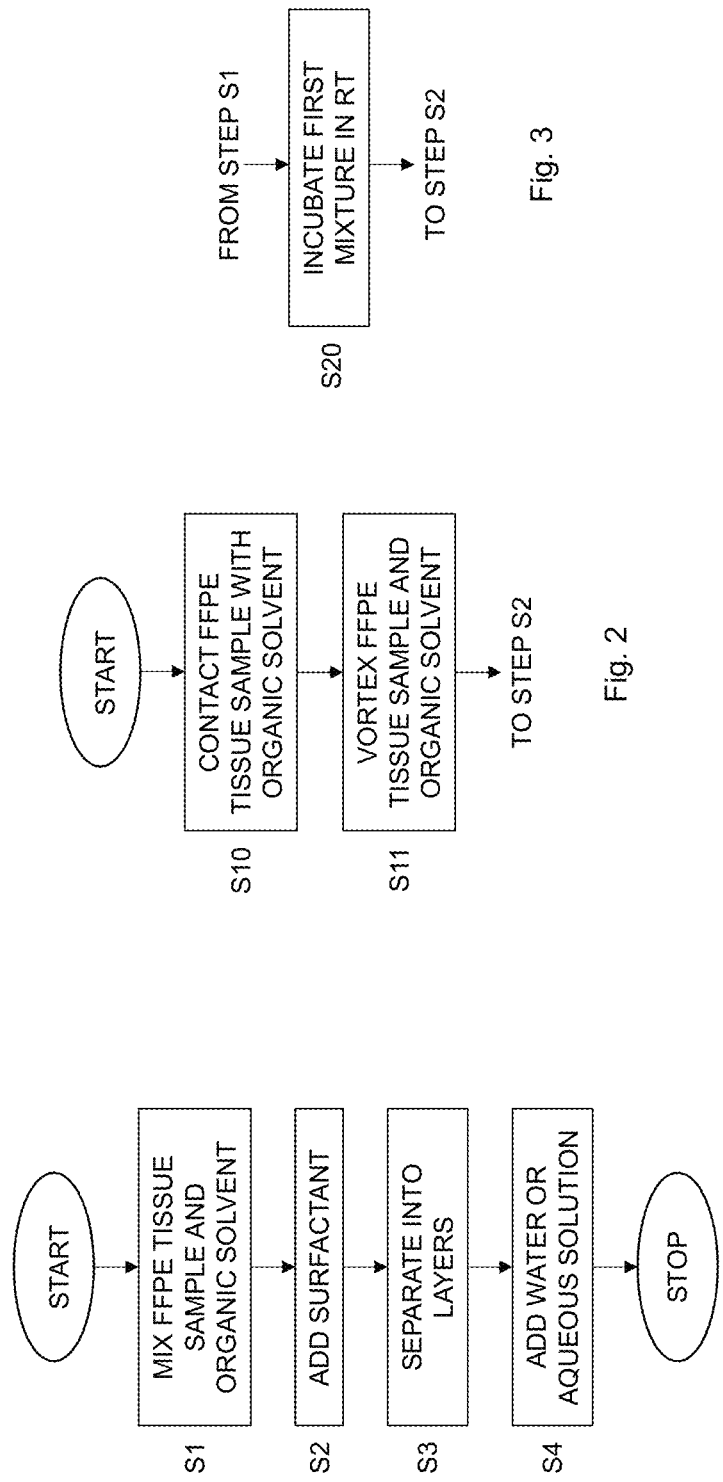

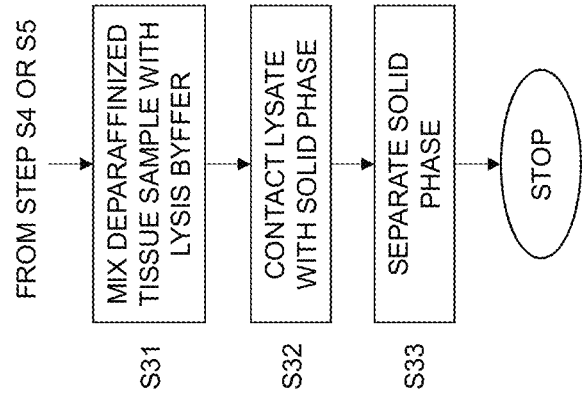
Fig. 6
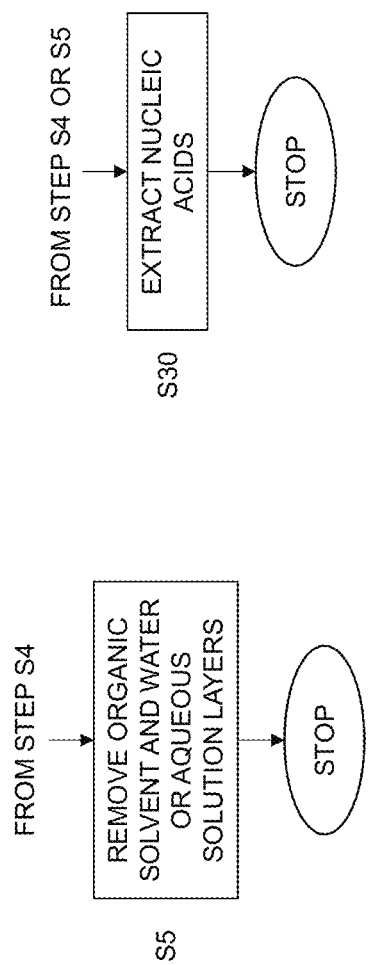
Fig. 5
Fig. 4

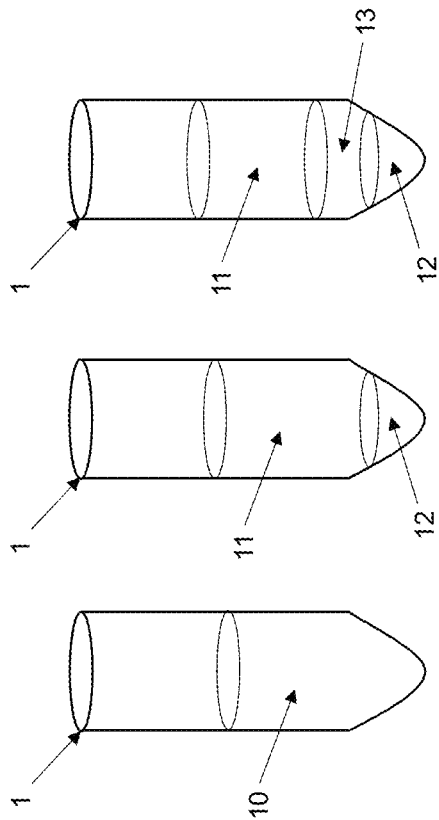
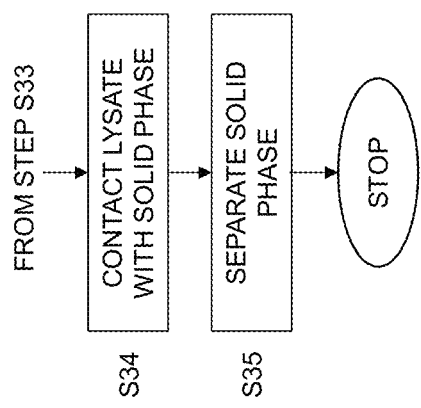

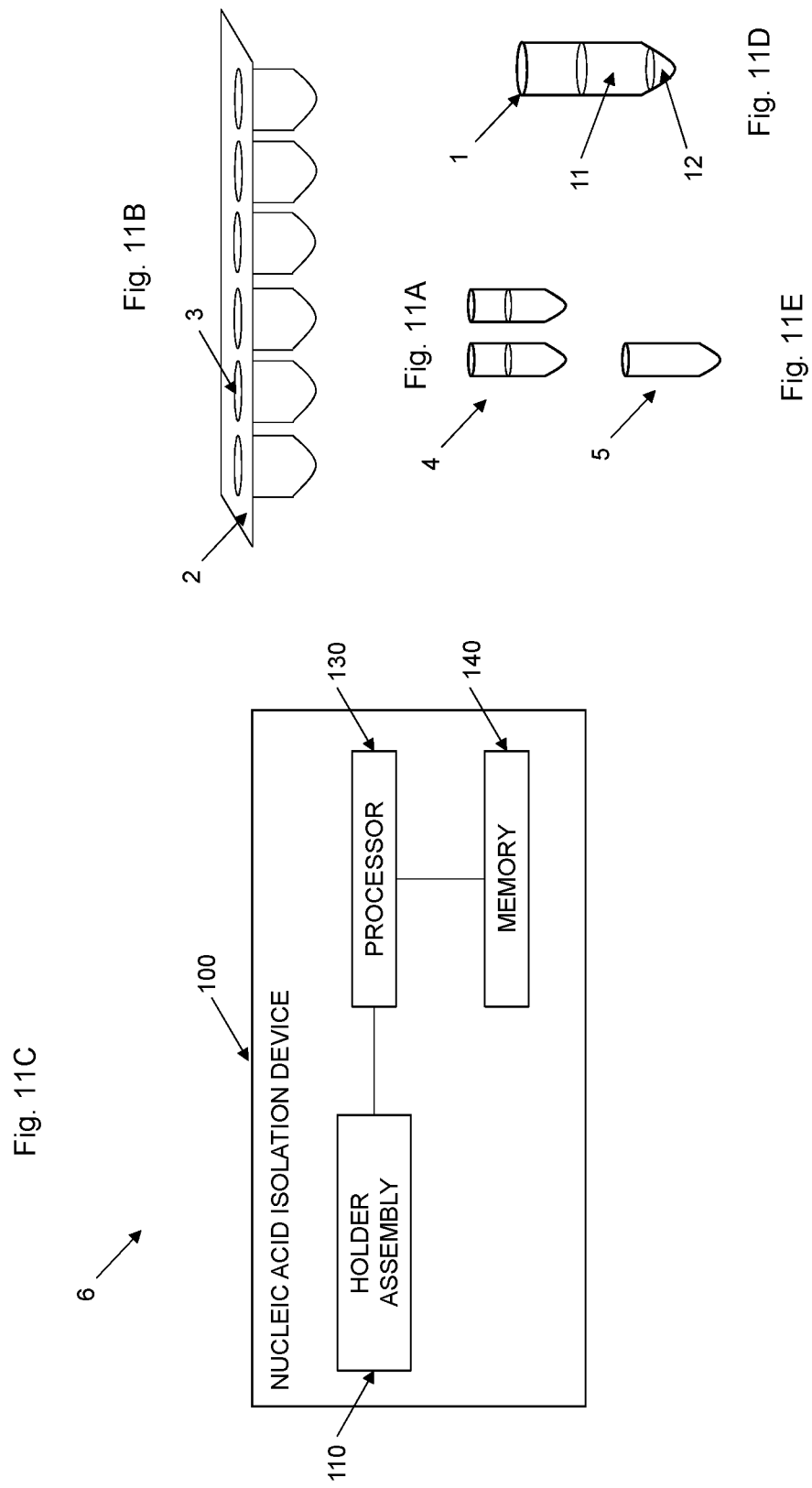

DEPARAFFINIZATION OF FFPE TISSUE SAMPLES

TECHNICAL FIELD

The present embodiments generally relate to deparaffinization of formalin-fixed paraffin-embedded (FFPE) tissue samples, and to such deparaffinization useful in connection with nucleic acid extraction.

BACKGROUND

The most common method for long-term preservation of diagnostic tissue samples and specimen is formalin-fixation and paraffin-embedding. Molecular research and diagnostics are constantly dependent on robust and time-effective methods for extraction of high quality nucleic acids from tissue samples, in particular FFPE tissue samples. There are, however, challenges with regard to isolating nucleic acids in high yield, integrity and purity from FFPE tissue samples.

Standard methods for isolation of nucleic acids from FFPE tissue samples are time-consuming, often requiring overnight digestions.

U.S. Pat. No. 8,574,868 discloses a method for deparaffinizing an FFPE tissue. The method comprises mixing an FFPE tissue sample with an organic solvent and water or with an organic solvent and an aqueous solution. The density of the organic solvent is less than that of the water or the aqueous solution and the organic solvent is immiscible with the water or the aqueous solution. The resulting mixture is separated into an organic solution layer and an aqueous solution layer. Paraffin dissolved from the FFPE tissue sample is present in the organic solution layer and the deparaffinized tissue is in the aqueous solution layer and/or in an intermediate layer between the organic solution layer and the aqueous solution layer.

SUMMARY

It is a general objective to provide an efficient deparaffinization of FFPE tissue samples.

It is a particular embodiment to provide a deparaffinization of FFPE tissue samples useful in connection with nucleic acid extraction.

These and other objectives are met by embodiments as disclosed herein.

An aspect of the embodiments relates to a method for deparaffinizing an FFPE tissue sample. The method comprising mixing the FFPE tissue sample with an organic solvent to form a first mixture. A surfactant is added to the first mixture to form a second mixture. The second mixture is then separated into an organic solvent layer and a surfactant layer. The surfactant layer comprises a deparaffinized tissue sample from the FFPE tissue sample. The method also comprises adding water or an aqueous solution to the separated second mixture to form an organic solvent layer, a water or aqueous solution layer and a surfactant layer. This surfactant layer comprises the deparaffinized tissue sample.

Another aspect of the embodiments relates to a kit for deparaffinizing an FFPE tissue sample. The kit comprises an organic solvent to be mixed with the FFPE tissue sample to form a first mixture, a surfactant to be added to the first mixture to form a second mixture and water or an aqueous solution to be added to the second mixture to form an organic solvent layer, a water or aqueous solution layer and a surfactant layer. The surfactant layer comprises the deparaffinized tissue sample.

A further aspect of the embodiments relates to a system for extracting nucleic acids from an FFPE tissue sample. The system comprises a container comprising an organic solvent and a container comprising a surfactant. The system also comprises a cartridge pre-filled, in respective cartridge containers, with a lysis buffer, a protease enzyme, magnetic beads that binds to nucleic acids, a binding buffer, ethanol, an elution buffer and water or an aqueous solution. The system comprises a nucleic acid isolation device. The nucleic acid isolation device comprises a holder assembly configured to carry the cartridge, a sample container comprising a deparaffinized tissue sample present in a surfactant layer separated from an organic solvent layer, and a nucleic acid collection container. The surfactant layer comprises the surfactant and the organic solvent layer comprises the organic solvent. The nucleic acid isolation device also comprises a processor and a memory. The memory comprises instructions executable by the processor to cause the processor to add water or the aqueous solution from the cartridge when carried by the holder assembly to the sample container when carried by the holder assembly to form an organic solvent layer, a water or aqueous solution layer and a surfactant layer. The surfactant layer comprises the deparaffinized tissue sample. The processor is also caused to remove the organic solvent layer and the water or aqueous solution layer from the sample container when carried by the holder assembly and add the lysis buffer from the cartridge when carried by the holder assembly to the sample container when carried by holder assembly to form a lysate. The processor is further caused to add the protease enzyme from the cartridge when carried by the holder assembly to the sample container when carried by the holder assembly and add the magnetic beads from the cartridge when carried by the holder assembly to the sample container when carried by the holder assembly. The processor is additionally caused to add the binding buffer from the cartridge when carried by the holder assembly to the sample container when carried by the holder assembly and add ethanol from the cartridge when carried by the holder assembly to the sample container when carried by the holder assembly. The processor is also caused to separate the magnetic beads from the lysate and add the elution buffer from the cartridge when carried by the holder assembly to the magnetic beads to collect the nucleic acids in the nucleic acid collection container when carried by the holder assembly.

A further aspect of the embodiments relates to a system for extracting nucleic acids from a FFPE tissue sample. The system comprises a container comprising an organic solvent, a container comprising a surfactant, a solid phase that binds to nucleic acids, a cartridge pre-filled, in respective cartridge containers, with a lysis buffer, a protease enzyme, a binding buffer, ethanol, an elution buffer and water or an aqueous solution, and a nucleic acid isolation device. The nucleic acid isolation device comprises a holder assembly configured to carry the cartridge, the solid phase, a sample container comprising a deparaffinized tissue sample present in a surfactant layer separated from an organic solvent layer, and a nucleic acid collection container. The surfactant layer comprises the surfactant and the organic solvent layer comprises the organic solvent. The nucleic acid isolation device also comprises a processor and a memory comprising instructions executable by the processor to cause the processor to add the water or aqueous solution from the cartridge when carried by the holder assembly to the sample container when carried by the holder assembly to form an organic solvent layer, a water or aqueous solution layer and a surfactant layer, wherein the surfactant layer comprises the deparaffinized tissue sample. The processor is further caused to remove the organic solvent layer and the water or aqueous solution layer from the sample container when carried by the holder assembly and add the lysis buffer from the cartridge when carried by the holder assembly to the sample container when carried by the holder assembly to form a lysate. The processor is additionally caused to add the protease enzyme from the cartridge when carried by the holder assembly to the sample container when carried by the holder assembly, add the binding buffer from the cartridge when carried by the holder assembly to the sample container when carried by the holder assembly, and add the ethanol from the cartridge when carried by the holder assembly to the sample container when carried by the holder assembly. The processor is additionally caused to contact the solid phase when carried by the holder assembly with the lysate from the sample container when carried by the holder assembly. The processor is also caused to add the elution buffer from the cartridge when carried by the holder assembly to the solid phase to collect the nucleic acids in the nucleic acid collection container when carried by the holder assembly.

Yet another aspect of the embodiments relates to a computer program comprising instructions, which when executed by a processor, cause the processor to add water or an aqueous solution from a pre-filled cartridge to a sample container comprising a deparaffinized tissue sample present in a surfactant layer comprising a surfactant separated from an organic solvent layer comprising an organic solvent. The processor is also caused to remove the organic solvent layer and a water or aqueous solution layer from the sample container and add a lysis buffer from the pre-filled cartridge to the sample container to form a lysate. The processor is further caused to add a protease enzyme from the pre-filled cartridge to the sample container and add magnetic beads from the pre-filled cartridge to the sample container. The processor is additionally caused to add a binding buffer from the pre-filled cartridge to the sample container and add ethanol from the pre-filled cartridge to the sample container. The processor is also caused to separate the magnetic beads from the lysate and add an elution buffer from the pre-filled cartridge to the magnetic beads to collect the nucleic acids in a nucleic acid collection container.

A further aspect of the embodiments relates to a computer program comprising instructions, which when executed by a processor, cause the processor to add water or an aqueous solution from a pre-filled cartridge to a sample container comprising a deparaffinized tissue sample present in a surfactant layer comprising a surfactant separated from an organic solvent layer comprising an organic solvent. The processor is also caused to remove the organic solvent layer and a water or aqueous solution layer from the sample container, add a lysis buffer from the pre-filled cartridge to the sample container to form a lysate and add a protease enzyme from the pre-filled cartridge to the sample container. The processor is further caused to add a binding buffer from the pre-filled cartridge to the sample container and add ethanol from the pre-filled cartridge to the sample container. The processor is additionally caused to contact a solid phase with the lysate from the sample container and add an elution buffer from the pre-filled cartridge to the solid phase to collect the nucleic acids in a nucleic acid collection container.

A related aspect of the embodiments defines a carrier comprising a computer program according to above. The carrier is preferably a computer-readable storage medium.

BRIEF DESCRIPTION OF THE DRAWINGS

The embodiments, together with further objects and advantages thereof, may best be understood by making reference to the following description taken together with the accompanying drawings, in which:

FIG. 1 is a flow chart illustrating a method for deparaffinizing an FFPE tissue sample;

FIG. 2 is a flow chart illustrating an embodiment of the mixing step in FIG. 1;

FIG. 3 is a flow chart illustrating an additional, optional step of the method shown in FIG. 1 according to an embodiment;

FIG. 4 is a flow chart illustrating an additional, optional step of the method shown in FIG. 1 according to another embodiment;

FIG. 5 is a flow chart illustrating an additional, optional step of the method shown in FIG. 1 according to a further embodiment;

FIG. 6 is a flow chart illustrating an embodiment of the extracting step in FIG. 5;

FIG. 7 is a flow chart illustrating additional, optional steps of the method shown in FIG. 6 according to an embodiment;

FIGS. 8A to 8C illustrate schematic sample tubes with a first mixture of FFPE tissue sample and organic solvent (FIG. 8A), organic solvent and surfactant layers (FIG. 8B) and organic solvent, water and aqueous solution and surfactant layers (FIG. 8C);

FIGS. 11A-11E schematically illustrate a system for extracting nucleic acids from an FFPE tissue sample according to an embodiment.

DETAILED DESCRIPTION

Figure 9C:
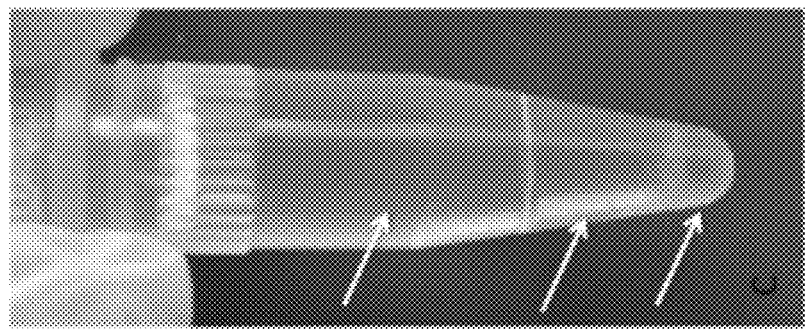
FIGS. 9A to 9C illustrate sample tubes with a first mixture of FFPE tissue sample and organic solvent (FIG. 9A), organic solvent and surfactant layers (FIG. 9B) and organic solvent, water and aqueous solution and surfactant layers (FIG. 9C)

The present embodiments generally relate to deparaffinization of formalin-fixed paraffin-embedded (FFPE) tissue samples, and to such deparaffinization useful in connection with nucleic acid extraction.

The embodiments provide a deparaffinizing method and kit that are fast and do not require any overnight digestions as many prior art deparaffinizing methods and kits. In addition, the integrity and quality of the resulting deparaffinized tissue sample is well maintained allowing the tissue sample to be used for various purposes following deparaffinization. For instance, a tissue sample deparaffinized according to the embodiments can be used for isolating nucleic acids in high yield, high integrity and high purity.

FIG. 1 is a flow chart illustrating a method for deparaffinizing an FFPE tissue sample according to an embodiment. The method comprising mixing the FFPE tissue sample with an organic solvent in step S1 to form a first mixture. A surfactant is added to the first mixture in step S2 to form a second mixture. The second mixture is then separated in step S3 into an organic solvent layer and a surfactant layer. The surfactant layer comprises a deparaffinized tissue sample from the FFPE tissue sample. A following step S4 comprises adding water or an aqueous solution to the separated second mixture to form an organic solvent layer, a water or aqueous solution layer and a surfactant layer. This surfactant layer comprises the deparaffinized tissue sample.

The method as shown in FIG. 1 and described above can generally be applied to any FFPE tissue sample. Generally, the FFPE tissue sample is in the form of a comparatively thin slice of FFPE tissue sample. Such slices generally have a thickness in the μm-range, i.e., ranging from one or few micrometers up to tens or hundreds of micrometers. In a typical embodiment, the FFPE tissue samples have a thickness of from 1 μm up to 100 μm, such as from 1 μm up to 50 μm or from 1 μm up to 25 μm, for instance about 10 μm. However, the embodiments are not limited to these illustrative, but non-limiting examples, of FFPE tissue sample thicknesses.

The tissue fixated in FFPE could be any tissue, part of organ or cluster of cells from any biological origin.

According to the embodiments, the organic solvent mixed with the FFPE tissue sample is capable of dissolving the paraffin out from the FFPE tissue sample. Accordingly, the paraffin from the FFPE tissue sample is dissolved in the organic solvent.

The surfactant is added in step S2 to collect the tissue sample, which thereby is present in the form of a deparaffinized tissue sample in the surfactant layer. The surfactant not only captures and collects the deparaffinized tissue sample. As is shown in the example section, the surfactant also improves the purity of the tissue sample by removing impurities. In addition, the surfactant improves the further processing of the tissue sample, and in particular results in improvements when extracting nucleic acids from the deparaffinized tissue sample. Thus, as is shown in the example section, absence of any surfactant resulted in failed separation of magnetic beads from a tissue lysate.

The addition of water or the aqueous solution provides a "safety layer" where, in order to ensure the complete removal of the upper organic solvent layer. The intermediate water or aqueous solution layer thereby constitutes an effective protection when removing the organic solvent layer to minimize removal of any tissue from the lower surfactant layer.

Furthermore, water soluble impurities are captured in the water or aqueous solution layer, whereas non-polar impurities are captured in the organic solvent layer.

FIG. 2 is a flow chart illustrating a particular embodiment of the mixing step S1 in FIG. 1. In this particular embodiment, the FFPE tissue sample is contacted with the organic solvent in step S10. The FFPE tissue sample and the organic solvent are then vortexed to form the first mixture. The method then continues to step S2 in FIG. 2.

In an embodiment, the FFPE tissue sample is added to a container, such as microtube or sample tube, and the organic solvent is added to the container in step S10. Alternatively, the organic solvent is added first to the container in step S10 followed by the FFPE tissue sample.

The container with the FFPE tissue sample and the organic solvent is then vortexed in step S11 to effectively mix the organic solvent and the FFPE tissue sample. In an illustrative example, the FFPE tissue sample and the organic solvent is vortexed in step S11 for one or a few seconds up to about one minute, such as from 2 s up to 30 s, or from 5 s up to 20 s, such as about 10 s.

FIG. 3 illustrates an additional, optional step of the method shown in FIG. 1. The method continues from step S1 in FIG. 1 or step S11 in FIG. 2. A next step S20 comprises incubating the first mixture in room temperature (RT, about 20° C. to 25° C.) for a time period selected within an interval of from 5 minutes up to 120 minutes prior to adding the surfactant to the first mixture in step S2 of FIG. 1.

In an embodiment, the incubation in step S20 takes place for a time period selected within an interval of from 10 minutes up to 60 minutes, preferably from 15 minutes up to 45 minutes, such as about 30 minutes.

The incubation of the first mixture in step S20 is optional and may be omitted. However, it may be advantageous to perform the incubation in order to efficiently dissolve the paraffin from the FFPE tissue sample into the organic solvent. Such incubation in step S20 is in particular preferred for FFPE tissue samples with polymer-enriched paraffin.

In an embodiment, step S2 of FIG. 1 comprises adding a surfactant solution to the first mixture to form the second mixture.

Hence, in this embodiment the surfactant is provided as a surfactant solution, in which the surfactant is dissolved in a suitable solvent.

In a particular embodiment, the concentration of the surfactant in the surfactant solution is selected so that the surfactant is not soluble in water or in the aqueous solution added in step S4. Thus, in this particular embodiment, the concentration of the surfactant in the surfactant solution is sufficiently high to not be soluble or be immiscible in water of the aqueous solution.

In another embodiment, the surfactant is in a pure form, i.e., not necessarily dissolved in any solvent.

In an embodiment, step S3 of FIG. 1 comprises separating the second mixture into the organic solvent layer comprising paraffin from the FFPE tissue sample and the surfactant layer comprising the deparaffinized tissue sample.

FIGS. 8A and 8B schematically illustrate this process. FIG. 8A illustrates a container 1, such as microtube or sample tube, comprising the first mixture 10 of the FFPE tissue sample and the organic solvent. FIG. 8B illustrates the container 1 following addition of the surfactant in step S2 and following separating the second mixture into the organic solvent layer 11 and the surfactant layer 12.

As is shown in FIG. 8B, the density of the surfactant is higher than that of the organic solvent so that the organic solvent layer 11 forms on the top with the surfactant layer 12 on the bottom.

Figure 9B:
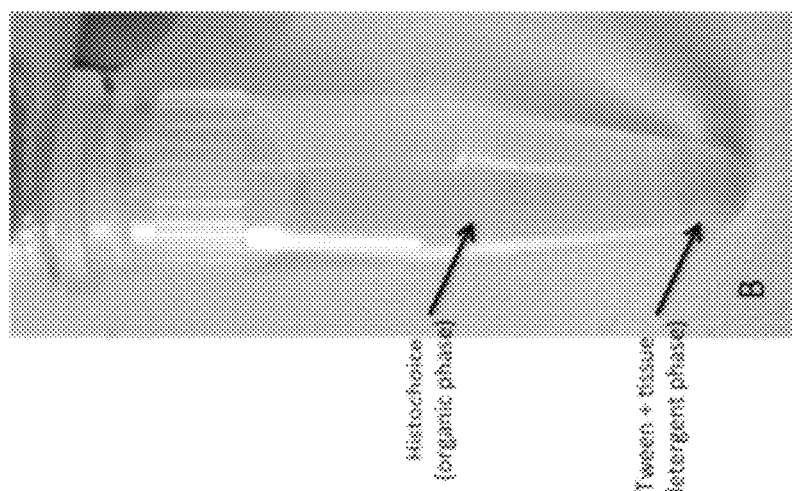
Figure 9A:
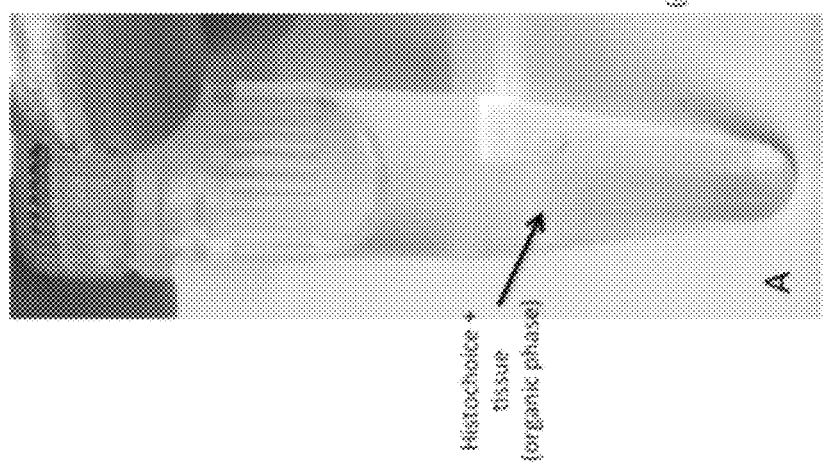

FIGS. 9A and 9B are photographs of a 1.5 ml microtube showing, in FIG. 9A, a first mixture of HISTOCHOICE® as organic solvent and an FFPE tissue sample. FIG. 9B illustrates the microtube once the second mixture has separated into the organic solvent layer (organic phase) comprising, in this example, HISTOCHOICE® with dissolved paraffin, and the surfactant layer (detergent phase) comprising, in this example, TWEEN® 20 as surfactant and the deparaffinized tissue sample.

In an embodiment, step S3 of FIG. 1 comprises centrifuging the second mixture at a rotational speed and centrifugation time sufficient to separate the second mixture into the organic solvent layer and the surfactant layer and collecting the deparaffinized tissue sample in the surfactant layer.

In a particular embodiment, the second mixture is centrifuged at a rotational speed selected within an interval of from 10,000×g up to 25,000×g and a centrifugation time selected within an interval of from 30 seconds up to 7 minutes.

For instance, the second mixture could be centrifuged in step S3 at a rotational speed selected within an interval of from 15,000×g up to 25,000×g, preferably from 17,500×g up to 22,500×g, such as about 20,000×g. Correspondingly, the centrifugation time is preferably selected within an interval of from 1 minute up to 5 minutes, more preferably from 1 minute up to 3 minutes, such as about 2 minutes.

Instead of, or as complement to, separating the second mixture by centrifugation in step S3, the separation of the second mixture into the organic solvent layer and the surfactant layer can be performed by incubating the second mixture in room temperature for a time period selected within an interval of from 1 minute up to 60 minutes.

In a particular embodiment, the second mixture is incubated in room temperature for a period of time selected within an interval of from 1 minute up to 45 minutes, preferably from 5 minutes up to 30 minutes.

In an embodiment, step S4 of FIG. 1 comprises adding water or the aqueous solution to the separated second mixture to form an upper organic solvent layer, an intermediate water or aqueous solution layer and a bottom surfactant layer. The bottom surfactant layer then comprises the deparaffinized tissue sample.

FIG. 8C schematically illustrates these three phases or layers 11, 12, 13 formed in a container 1. The upper layer is the organic solvent layer 11 comprising dissolved paraffin. The intermediate layer is the water or aqueous solution layer 13 and the bottom layer is the surfactant layer 12 comprising the deparaffinized tissue.

FIG. 9C is a photograph illustrating the upper organic solvent layer (organic phase) with HISTOCHOICE® and paraffin, water in the intermediate layer (aqueous phase) and the bottom surfactant layer (detergent phase) with TWEEN® 20 and the deparaffinized tissue sample.

Hence, in a preferred embodiment the density of the organic solvent is preferably lower than the density of water or the aqueous solution, which in turn is preferably lower than the density of the surfactant.

In a particular embodiment, the organic solvent has a density at room temperature within an interval of from 0.7 up to 0.9 g/ml, preferably within an interval of from 0.725 up to 0.875 g/ml, more preferably within an interval of from 0.75 up to 0.85 g/ml, such as within an interval of from 0.76 up to 0.82 g/ml or from 0.77 up to 0.795 g/ml.

In a particular embodiment, the surfactant has a density at room temperature of at least 1.05 g/ml, preferably at least 1.1 g/ml.

The aqueous solution, if used instead of water, preferably has a density close to that of water, i.e., about 1 g/ml. Preferably, the aqueous solution has a density higher than 0.85 g/ml, preferably higher than 0.875 g/ml and more preferably higher than 0.9 g/ml with the proviso that the density is higher than the density of the organic solvent. Correspondingly, the aqueous solution preferably has a density lower than 1.1 g/ml, preferably lower than 1.05 g/ml with the proviso that the density is lower than the density of the surfactant.

In a particular embodiment, step S4 comprises adding water to the separated second mixture to form the organic solvent layer, the water layer and the surfactant layer.

For instance, ultrapure water, such as water of Type 1 as defined by ISO 3696 could be added in step S4. An example of such ultrapure water is Milli-Q® (MQ) water.

In another particular embodiment, step S4 comprises adding an aqueous buffer solution to the separated second mixture to form the organic solvent layer, the aqueous solution layer and the surfactant layer.

Various aqueous buffer solutions could be used in this particular embodiment. Illustrative but non-limiting examples of such aqueous buffer solutions include tris (hydroxymethyl)aminomethane (Tris) and ethylenediaminetetraacetic acid (EDTA) (TE) aqueous buffer solutions.

FIG. 4 is a flow chart illustrating an additional, optional step S5. The method continues from step S4 in FIG. 1 to step S5. Step S5 comprise removing the organic solvent layer and the water or aqueous solution layer to retrieve the surfactant layer comprising the deparaffinized tissue sample.

The organic solvent layer and the water or aqueous solution layer can be removed using any suitable technique. As is shown in FIGS. 8C and 9C, these two layers constitute the two uppermost layers. Hence, a suitable technique for removing these layers is to pipette or otherwise draw up the organic solution and water or the organic solution and the aqueous solution, thereby leaving the surfactant layer with the deparaffinized tissue sample. Another technique is decanting or pouring off the two upper layers with the surfactant layer remaining in the container.

In a particular embodiment, the organic solvent is immiscible with water of the aqueous solution.

Illustrative, but non-limiting examples of organic solvents that can be used according to the embodiments is an organic solvent selected from a group consisting of xylene; toluene; a terpene, such as 2,6-dimethyl-2,4,6-octatriene; acids derived from unsubstituted or substituted cyclopentane, cyclopentene, cyclohexane and cyclohexene, preferably cyclopentanecarboxylic acid, cyclopentylacetic acid, alkyl-substituted cyclopentyl formic acid, alkyl-substituted cyclopentenyl formic acid, alkyl-substituted cyclohexyl formic acid, alkyl-substituted cyclohexenyl formic acid, alkenyl-substituted cyclopentyl formic acid, alkenyl-substituted cyclopentenyl formic acid, alkenyl-substituted cyclohexyl formic acid, alkenyl-substituted cyclohexenyl formic acid, alkyl-substituted cyclopentyl acetic acid, alkyl-substituted cyclopentenyl acetic acid, alkenyl-substituted cyclohexyl acetic acid, alkyl-substituted cyclohexenyl acetic acid, alkenyl-substituted cyclopentyl acetic acid, alkenyl-substituted acid, or alkenyl-substituted cyclohexenyl acetic acid; unsubstituted or substituted saturated forms of fluorene, phenanthrene, anthracene, p-terphenyl fluoranthene, pyrene or chrysene; and unsubstituted or substituted saturated or partially-saturated quinoline, isoquinoline, pyridine, indole, acridine, carbazole, tetramethylene or pentamethylene sulfides.

In a particular embodiment, the organic solvent is an organic solvent as defined in U.S. Pat. No. 5,344,637, i.e., consisting essentially of from 5% to 100% by weight of a compound or combination of compounds having a higher flashpoint than xylene and which is selected from the group consisting of unsubstituted and substituted saturated, organic ring-containing compounds, hydrogenated aromatic petroleum distillates, and combinations thereof. For instance, the organic solvent is an organic ring-containing compound selected from the group consisting of unsubstituted and substituted cyclopentane, cyclopentene, cyclohexane and cyclohexene, or acids derived from the organic ring-containing compound. In another example, the organic solvent is medium aliphatic solvent naphtha (petroleum) with CAS number 64742-88-7 or comprises 95% to 100% of medium aliphatic solvent naphtha (petroleum).

In another particular embodiment, the organic solvent is HISTOCHOICE® clearing agent, which is an aqueous mixture of ethanol and ethandial.

As previously mentioned herein, the surfactant preferably has a concentration selected so that the surfactant is not soluble in water or the aqueous solution. Thus, the surfactant is preferably immiscible in water or in the aqueous solution.

Surfactants are compounds that lower the surface tension, or interfacial tension, between two liquids or between a liquid and a solid. Surfactants may act as detergents, wetting agents, emulsifiers, foaming agents, and dispersants.

Surfactants may be anionic, cationic, zwitterionic or non-ionic surfactants. Preferred surfactants are non-ionic surfactants.

In a particular embodiment, the surfactant is a detergent.

A detergent is a surfactant that enables manipulation, such as disruption or formation, of hydrophobic-hydrophilic interactions among molecules in biological samples. Detergents are used to lyse cells, solubilize membrane proteins and lipids, control protein crystallization, prevent non-specific binding in affinity purification and immunoassay procedures, and as additives in electrophoresis. Detergents are generally amphiphilic, i.e., partly hydrophilic (polar) and partly hydrophobic (non-polar).

Detergents may, as surfactants, be anionic, cationic, zwitterionic or non-ionic detergents. Preferred detergents are non-ionic detergents.

In an embodiment, the surfactant is selected from a group consisting of diethanolamine, triethanolamine, octylphenoxypolyethoxyethanol and polysorbates. Preferred polysorbates include polysorbate 20, polysorbate 40, polysorbate 60 and polysorbate 80, more preferably polysorbate 20 or polysorbate 80. A currently preferred polysorbate is polysorbate 20.

Polysorbate 20, also referred to as polyoxyethylene (20) sorbitan monolaurate and TWEEN® 20, is a non-ionic detergent with a density of 1.1 g/ml in room temperature. It has a solubility in water in room temperature of 100 mg/ml.

Polysorbate 40, also referred to as polyoxyethylene (20) sorbitan monopalmitate and TWEEN® 40, is a non-ionic detergent with a density of 1.08-1.09 g/ml in room temperature.

Polysorbate 60, also referred to as polyoxyethylene (20) sorbitan monostearate and TWEEN® 60, is a non-ionic detergent with a density of 1.044 g/ml in room temperature.

Polysorbate 80, also referred to as polyoxyethylene (20) sorbitan monooleate and TWEEN® 80, is a non-ionic detergent with a density of 1.06-1.09 g/min in room temperature.

Diethanolamine, also referred to as 2,2'-iminodiethanol, is a non-ionic surfactant with a density of 1.097 g/ml in room temperature. It has a solubility in water in room temperature of 100 mg/ml.

Triethanolamine, also referred to as 2,2',2"-nitrilotri(ethan-1-ol), is a non-ionic detergent with a density of 1.124 g/ml.

Octylphenoxypolyethoxyethanol is a non-ionic detergent with a density of 1.07 g/ml in room temperature.

In an embodiment, step S1 of FIG. 1 comprises mixing the FFPE tissue sample with 600 µl to 1200 µl, preferably 800 µl to 1000 µl, more preferably about 950 µl organic solvent to form the first mixture. In an embodiment, step S2 comprises adding 20 µl to 100 µl, preferably 40 µl to 60 µl, more preferably about 50 µl surfactant to the first mixture to form the second mixture. In an embodiment, step S4 comprises adding 125 µl to 600 µl, preferably 150 µl to 400 µl, more preferably about 200 µl water or aqueous solution to the separated second mixture to form the organic solvent layer, the water or aqueous solution layer and the surfactant layer.

As mentioned in the foregoing, the method for deparaffinizing an FFPE tissue sample of the embodiments results in a deparaffinized tissue sample of high quality that may be used for various applications and purposes.

In a particular embodiment, nucleic acids are extracted from the deparaffinized tissue sample.

FIG. 5 is a flow chart illustrating an additional step useful in such an extraction embodiment. The method continues from step S4 in FIG. 1 or step S5 in FIG. 4. A next step S30 comprises extracting nucleic acids from the deparaffinized tissue sample.

Various nucleic acids species may be extracted from the deparaffinized tissue sample. In an embodiment, deoxyribonucleic acid (DNA) is extracted in step S30 from the deparaffinized tissue sample. In another embodiment, ribonucleic acid (RNA) is extracted in step S30 from the deparaffinized tissue sample. In a further embodiment, both DNA and RNA are extracted in step S30 from the deparaffinized tissue sample. In this latter embodiment, DNA and RNA could be extracted together forming a DNA and RNA mixture. Alternatively, DNA and RNA could be extracted separately, such as sequentially, to retrieve DNA and RNA separately.

FIG. 6 is a flow chart illustrating an embodiment of the extracting step in FIG. 5. In this embodiment, the extraction comprises mixing the deparaffinized tissue sample with a lysis buffer to form a lysate in step S31. The method also comprises contacting the lysate in step S32 with a solid phase that binds to the nucleic acids and then separating the solid phase from the lysate in step S33.

In an embodiment, the lysis buffer is a lysis buffer capable of lysing the cell membrane of the cells in the deparaffinized tissue sample. Accordingly, the lysate will then comprise, above all, RNA as nucleic acid species. In another embodiment, the lysis buffer is a lysis buffer capable of lysing not only the cell membrane of the cells but also the nucleus membrane of the cell nucleus of the cells. In this embodiment, the lysate will comprise a mixture of DNA and RNA.

Non-limiting examples of lysis buffers that can be used include NP-40 lysis buffers, radio immune precipitation assay (RIPA) lysis buffers, sodium dodecyl sulfate (SDS) lysis buffers, ammonium-chloride-potassium (ACK) lysis buffer as illustrative but non-limiting examples. Other examples of lysis buffers that can be used include buffers comprising guanidine thiocyanate and guanidine hydrochloride.

An example of a lysis buffer that can be used according to the embodiments comprises 100 nM NaCl, 500 mM Tric HCl, pH 8.0, 1% SDS.

In an embodiment, the lysis buffer comprises a protease enzyme, or the protease enzyme is added following addition of the lysis buffer. An example of such a protease enzyme is proteinase K.

The solid phase is preferably beads configured to bind to the nucleic acids, such as magnetic beads configured to bind to the nucleic acids. Magnetic beads simplify separating the solid phase from the lysate since the magnetic beads may be collected by a magnet. Such magnetic beads are typically coated with a nucleic acid binding material, such as silica. Other solid phases that can be used according to the embodiments include silica gel membranes, such as silica gel membranes in spin columns.

In a particular embodiment allowing extraction of both RNA and DNA, step S32 of FIG. 6 comprises contacting the lysate with a first solid phase that selectively binds to a first species of nucleic acids. The following step S33 comprises separating the first solid phase from the lysate to form a lysate depleted of the first species of nucleic acids. In this embodiment, the method comprises the additional steps as shown in FIG. 7. The following step S34 comprises contacting the lysate depleted of the first species of nucleic acids with a second solid phase that binds to a second species of nucleic acids. The second solid phase is then separated in step S35 from the lysate depleted of the first species of nucleic acids.

In an embodiment, the first species of nucleic acids is DNA and the second species of nucleic acids is RNA. In another embodiment, the first species of nucleic acids is RNA and the second species of nucleic acids is DNA.

In an embodiment, the first and second solid phases are magnetic beads. For instance, one of the solid phases could be MagPrep Silica HS beads that selectively binds DNA and the other solid phase may then be MagPrep Silica beads capable of binding RNA.

In an embodiment, a sequential extraction or isolation of nucleic acids as disclosed in U.S. Pat. No. 8,889,393 may be used.

The deparaffinized tissue samples obtained according to the embodiments can be further used in other applications than extraction or isolation of nucleic acids. For instance, deparaffinized tissue samples may be used for histology or histopathology to facilitate access of stains and dyes to tissue sample in order to visualize and highlight structures in biological tissues or quantify the presence of a specific compound or molecule in the tissue.

FFPE tissue may also be deparaffinized in order to extract protein from it for various biological analyses, e.g., using Western blot.

Another aspect of the embodiments relates to a kit for deparaffinizing an FFPE tissue sample. The kit comprises an organic solvent to be mixed with the FFPE tissue sample to form a first mixture, a surfactant to be added to the first mixture to form a second mixture and water or an aqueous solution to be added to the second mixture to form an organic solvent layer, a water or aqueous solution layer and a surfactant layer. The resulting surfactant layer comprises the deparaffinized tissue sample.

The kit optionally comprises respective containers or vessels, such as dials, microtubes, cartridges or other containers, comprising the chemicals of the kit. For instance, the kit could comprise a first container comprising the organic solvent, a second container comprising the surfactant and a third container comprising water or the aqueous solution.

In an embodiment, the first container comprises 600 µl to 1200 µl, preferably 800 µl to 1000 µl, more preferably 950 µl, of the organic solvent. The second container comprises, in an embodiment, 20 µl to 100 µl, preferably 40 µl to 60 µl, more preferably 50 µl, of the surfactant. In an embodiment, the third container comprises 125 µl to 600 µl, preferably 150 µl to 400 µl, more preferably 200 µl, of water or the aqueous solution.

In an embodiment, the kit also comprises instructions defining that the organic solvent is to be mixed with the FFPE tissue sample to form the first mixture, instructions defining that the surfactant is to be added to the first mixture to form the second mixture and instructions defining that water or the aqueous solution is to be added to the second mixture to form the organic solvent layer, the water of aqueous solution layer and the surfactant layer.

In an embodiment, the kit also comprises, optionally in separate containers or other vessels, a lysis buffer and a solid phase that binds to nucleic acids. The kit optionally also comprises a protease enzyme. In this embodiment, the kit is used not only for deparaffinizing an FFPE tissue sample but also for extracting nucleic acids from the tissue sample following deparaffinization.

In an embodiment, the kit comprises a first solid phase that selectively binds to a first species of nucleic acids and a second solid phase that binds to a second species of nucleic acids.

The first and second solid phases are preferably beads, such as magnetic beads, or spin columns configured to bind to nucleic acids.

The kit optionally also comprise at least one of a binding buffer, a wash buffer, an elution buffer and ethanol as further described herein.

A further aspect of the embodiments relates to, see FIGS. 11A-11E, a system 6 for extracting nucleic acids from an FFPE tissue sample. The system 6 comprises a container 4 comprising an organic solvent and a container 4 comprising a surfactant. The system 6 also comprises a cartridge 2 pre-filled, in respective cartridge containers 3, with a lysis buffer, a protease enzyme, magnetic beads that binds to nucleic acids, a binding buffer, ethanol, an elution buffer and water or an aqueous solution. The system 6 of the embodiments comprises a nucleic acid isolation device 100. The nucleic acid isolation device 100 comprises a holder assembly 110 configured to carry the cartridge 2 and to carry a sample container 1 comprising a deparaffinized tissue sample present in a surfactant layer 12 separated from an organic solvent layer 11. As previously mentioned herein, the surfactant layer 12 comprises the surfactant and the organic solvent layer 11 comprises the organic solvent. The holder assembly 110 is also configured to carry a nucleic acid collection container 5. The nucleic acid isolation device 100 also comprises a processor 130 and a memory 140.

The holder assembly 110 can be implemented according to different embodiments. In a first embodiment, the holder assembly 110 could be in the form of rack carrying the cartridge 2, the sample container 1 and the nucleic acid collection container 5. For instance, the cartridge 2 could comprise container carrying structures configured to carry the sample container 1 and the nucleic acid collection container 5. In another embodiment, the cartridge 2 comprises a container carrying structure configured to carry one of the containers 1, 5 with the other container 1, 5 carried by another part of the holder assembly 110, such as a container or tube rack. In a further embodiment, the holder assembly 110 comprises one structure, such as cartridge rack, configured to carry the cartridge 2, and one structure, such as container or tube track, configured to carry the containers 1, 5. In yet another embodiment, the holder assembly 110 comprises a first structure, such as cartridge rack, configured to carry the cartridge 2, a second structure, such as container or tube track, configured to carry the sample container 1, and a third structure, such as container or tube track, configured to carry the nucleic acid collection container 5.

The memory 140 comprises instructions executable by the processor 130 to cause the processor 130 to perform a nucleic acid extraction or isolation process as described herein. Thus, the processor 130 is caused to add water or the aqueous solution from the cartridge 2 when carried by the holder assembly 110 to the sample container 1 when carried by the holder assembly 110 to form an organic solvent layer, a water or aqueous solution layer and a surfactant layer. The surfactant layer comprises the deparaffinized tissue sample. The processor 130 is also caused to remove the organic solvent layer and the water or aqueous solution layer from the sample container 1 when carried by the holder assembly 110 and add the lysis buffer from the cartridge 2 when carried by the holder assembly 110 to the sample container 1 when carried by the holder assembly 110 to form a lysate. The processor 130 is further caused to add the protease enzyme from the cartridge 2 when carried by the holder assembly 110 to the sample container 1 when carried by the holder assembly 110 and add the magnetic beads from the cartridge 2 when carried by the holder assembly 110 to the sample container 1 when carried by the holder assembly 110. The processor 130 is additionally caused to add the binding buffer from the cartridge 2 when carried by the holder assembly 110 to the sample container 1 when carried by the holder assembly 110 and add ethanol from the cartridge 2 when carried by the holder assembly 110 to the sample container 1 when carried by the holder assembly 110. The processor 130 is also caused to separate the magnetic beads from the lysate and add the elution buffer from the cartridge 2 when carried by the holder assembly 110 to the magnetic beads to collect the nucleic acids in the nucleic acid collection container 5 when carried by the holder assembly 110.

Non-limiting, but illustrative, examples of nucleic acid isolation devices 100 that can be used in the system 6 include MAGTRATION® System 6GC, MAGTRATION® System 12GC PLUS, magLEAD® 6gC and magLEAD® 12gC. Generally, any liquid handling robotic workstation capable of handling volumes of chemicals as described in the foregoing could be used in the system 6. Examples of such workstations include Janus G3* Varispan Automated Workstation, Janus G3* Varispan MDT Automated Workstation, and Janus G3* MDT Automated Workstation by Perkin Elmer; liquid handling workstations from Tecan; VANTAGE LIQUID HANDLING SYSTEM®, MICROLAB® STAR Line and MICROLAB® NIMBUS by Hamilton.

The processor 130 and the memory 140 are interconnected to each other to enable normal software execution. The processor 130 is preferably also connected to equipment arranged in connection with the holder assembly 110 in order to retrieve chemicals or agents from the cartridge containers 3 of the cartridge 2 when carried by the holder assembly 110 and from the sample container 1 when carried by the holder assembly 110 and to add chemicals or agents into the sample container 1 when carried by the holder assembly 110 and into the nucleic acid collection container 5 when carried by the holder assembly 110.

In an embodiment, the cartridge 2 is pre-filled, in respective cartridge containers 3, with the lysis buffer, the protease enzyme, the magnetic beads that binds to nucleic acids, the binding buffer, a wash buffer, ethanol, the elution buffer and water or the aqueous solution. In this embodiment, the memory 140 comprises instructions executable by the processor 130 to cause the processor 130 to wash the magnetic beads with the wash buffer from the cartridge 2 when carried by the holder assembly 110.

In an embodiment, the cartridge 2 is pre-filled, in respective cartridge containers 3, with the lysis buffer, the protease enzyme, first magnetic beads that selectively binds to a first species of nucleic acids, the binding buffer, ethanol, the wash buffer, the elution buffer, second magnetic beads that binds to a second species of nucleic acids, and water or the aqueous solution. In this embodiment, the holder assembly 110 is configured to carry a first nucleic acid collection container 5 and a second nucleic acid collection container 5. The memory 140 comprises, in this embodiment, instructions executable by the processor 130 to cause the processor 130 to add the first magnetic beads from the cartridge 2 when carried by the holder assembly 110 to the sample container 1 when carried by the holder assembly 110. The processor 130 is also caused to separate the first magnetic beads from the lysate and wash the first magnetic beads with the binding buffer and with the wash buffer from the cartridge 2 when carried by the holder assembly 110. The processor 130 is further caused to add the elution buffer from the cartridge 2 when carried by the holder assembly 110 to the first magnetic beads to collect the first species of nucleic acids in the first nucleic acid collection container 5 when carried by the holder assembly 110. The processor 130 is also caused to add the second magnetic beads from the cartridge 2 when carried by the holder assembly 110 to the sample container 1 when carried by the holder assembly 110 and separate the second magnetic beads from the lysate. The processor 130 is further caused to wash the second magnetic beads with the wash buffer from the cartridge 2 when carried by the holder assembly 110 and add the elution buffer from the cartridge 2 when carried by the holder assembly 110 to the second magnetic beads to collect the second species of nucleic acids in the second nucleic acid collection container 5 when carried by the holder assembly 110.

In another embodiment, magnetic beads are not necessarily used as the solid phase. For instance, a spin column or other column comprising nucleic acid binding material could instead be used. The system 6 then comprises a solid phase that binds to nucleic acids and cartridge 2 does not need to contain any magnetic beads. In this embodiment, the holder assembly 110 is configured to carry the solid phase, such as in rack together with the cartridge 2 and/or containers 4, 5 or in a separate holder. In this embodiment, the memory 140 comprises instructions executable by the processor 130 to cause the processor 130 to add the water or aqueous solution from the cartridge 2 when carried by the holder assembly 110 to the sample container 1 when carried by the holder assembly 110 to form an organic solvent layer, a water or aqueous solution layer and a surfactant layer, wherein the surfactant layer comprises the deparaffinized tissue sample. The processor 130 is further caused to remove the organic solvent layer and the water or aqueous solution layer from the sample container 1 when carried by the holder assembly 110 and add the lysis buffer from the cartridge 2 when carried by the holder assembly 110 to the sample container 1 when carried by the holder assembly 110 to form a lysate. The processor 130 is additionally caused to add the protease enzyme from the cartridge 2 when carried by the holder assembly 110 to the sample container 1 when carried by the holder assembly 110, add the binding buffer from the cartridge 2 when carried by the holder assembly 110 to the sample container 1 when carried by the holder assembly 110, and add the ethanol from the cartridge when carried by the holder assembly 110 to the sample container 1 when carried by the holder assembly 110. The processor 1 is additionally caused to contact the solid phase when carried by the holder assembly 110 with the lysate from the sample container 1 when carried by the holder assembly 110. The processor 110 is also caused to add the elution buffer from the cartridge 2 when carried by the holder assembly 110 to the solid phase to collect the nucleic acids in the nucleic acid collection container 5 when carried by the holder assembly 110.

The term 'processor' should be interpreted in a general sense as any system or device capable of executing program code or computer program instructions to perform a particular processing, determining or computing task.

The processor does not have to be dedicated to only execute the above-described steps, functions, procedure and/or blocks, but may also execute other tasks.

Figure 12:
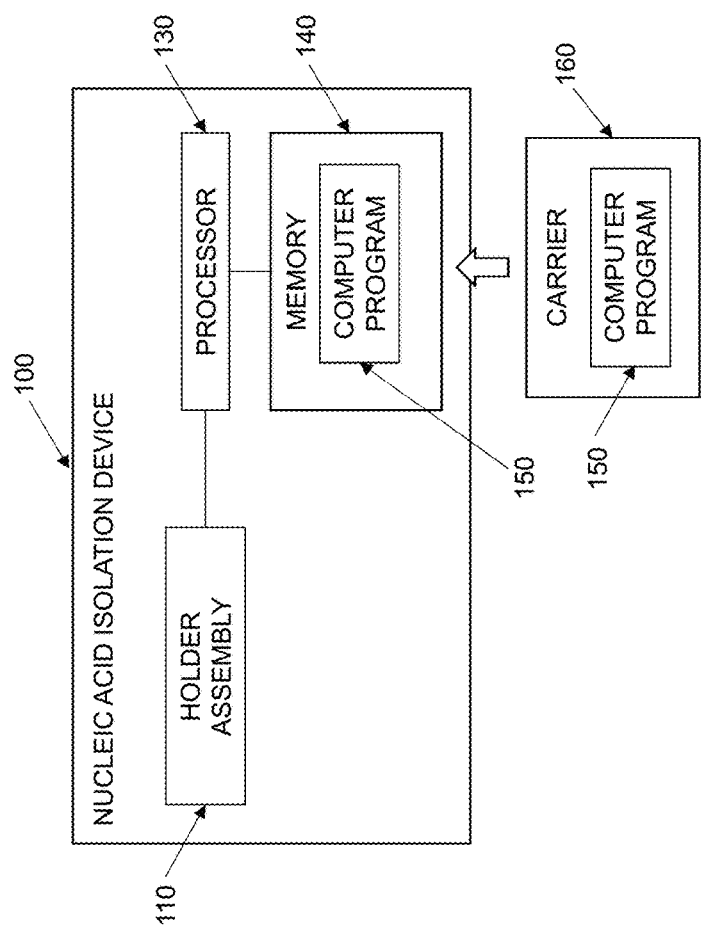
FIG. 12 schematically illustrates a nucleic acid isolation device and a computer program according to an embodiment.

FIG. 12 illustrates a schematic implementation of the nucleic acid isolation device 100 with a computer program 150 carried by carrier 160 loaded into the memory 140 of the nucleic acid isolation device 100.

In an embodiment, the computer program 150 comprises instructions, which when executed by a processor 130, cause the processor 130 to add water or an aqueous solution from a pre-filled cartridge 2 to a sample container 1 comprising a deparaffinized tissue sample present in a surfactant layer 12 comprising a surfactant separated from an organic solvent layer 11 comprising an organic solvent. The processor 130 is also caused to remove the organic solvent layer 11 and a water or aqueous solution layer 13 from the sample container 1 and add a lysis buffer from the pre-filled cartridge 2 to the sample container 1 to form a lysate. The processor 130 is further caused to add a protease enzyme from the pre-filled cartridge 2 to the sample container 1 and add magnetic beads from the pre-filled cartridge 2 to the sample container 1. The processor 130 is additionally caused to add a binding buffer from the pre-filled cartridge 2 to the sample container 1 and add ethanol from the pre-filled cartridge 2 to the sample container 1. The processor 130 is also caused to separate the magnetic beads from the lysate and add an elution buffer from the pre-filled cartridge 2 to the magnetic beads to collect the nucleic acids in a nucleic acid collection container 5.

In an embodiment, the computer program 140 also comprises instructions, which when executed by the processor 130, cause the processor 130 to wash the magnetic beads with a wash buffer from the pre-filled cartridge 2.

In an embodiment, the computer program 140 further comprises instructions, which when executed by the processor 130, cause the processor 130 to add first magnetic beads from the pre-filled cartridge 2 to the sample container 1 and separate the first magnetic beads from the lysate. The processor 130 is also caused to wash the first magnetic beads with the binding buffer and with the wash buffer from the pre-filled cartridge 2 and add the elution buffer from the pre-filled cartridge 2 to the first magnetic beads to collect a first species of nucleic acids in a first nucleic acid collection container 5. The processor 130 is further caused to add second magnetic beads from the pre-filled cartridge 2 to the sample container 1 and separate the second magnetic beads from the lysate. The processor 130 is also caused to wash the second magnetic beads with the wash buffer from the pre-filled cartridge 2 and add the elution buffer from the pre-filled cartridge 2 to the second magnetic beads to collect a second species of nucleic acids in a second nucleic acid collection container 5.

In another embodiment, the computer program 150 comprises instructions, which when executed by a processor 130, cause the processor 130 to add water or an aqueous solution from a pre-filled cartridge 2 to a sample container 1 comprising a deparaffinized tissue sample present in a surfactant layer 12 comprising a surfactant separated from an organic solvent layer 11 comprising an organic solvent. The processor 130 is also caused to remove the organic solvent layer 11 and a water or aqueous solution layer 13 from the sample container 1, add a lysis buffer from the pre-filled cartridge 2 to the sample container 1 to form a lysate and add a protease enzyme from the pre-filled cartridge 2 to the sample container 1. The processor 130 is further caused to add a binding buffer from the pre-filled cartridge 2 to the sample container 1 and add ethanol from the pre-filled cartridge 2 to the sample container 1. The processor 130 is additionally caused to contact a solid phase with the lysate from the sample container 1 and add an elution buffer from the pre-filled cartridge 2 to the solid phase to collect the nucleic acids in a nucleic acid collection container 5.

The proposed technology also provides a carrier 160 comprising the computer program 150. The carrier 160 is preferably a computer-readable storage medium.

By way of example, the software or computer program 150 may be realized as a computer program product, which is normally carried or stored on a computer-readable medium 160, in particular a non-volatile medium. The computer-readable medium 160 may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program 150 may thus be loaded into the operating memory 140 of the nucleic acid isolation device 100 for execution by the processor 130 thereof.

In a particular embodiment, the carrier 160 is a smart card, chip card, or integrated circuit card.

EXAMPLES

Example 1

This example illustrates the usage of xylene as organic solvent and TWEEN® 20 as surfactant.

Deparaffinization

Two slices (thickness 10 μm) of formalin-fixed, paraffin-embedded (FFPE) tissue sample from duplicate brain specimens were placed into a microcentrifuge tube. 950 μl of 100% xylene was added to the microcentrifuge tube and mixed with the sample by vortexing for 10 seconds. 50 μl of TWEEN® 20 was then added to the mixture and the sample was centrifuged for 2 minutes at 20,000×g. Next, 200 μl of MQ water was added to the tube, creating a third phase between the organic solvent and surfactant. 1 ml of liquid was then removed from the upper layers of liquid (organic phase and water) to leave a lower layer containing deparaffinized tissue.

Extraction 180 μl of a lysis buffer (100 mM NaCl, 500 mM Tris HCl pH 8.0, 1% SDS) was added to the sample, followed by 40 μl of Proteinase K (20 mg/ml) mixed and incubated for 40 minutes-2 hours at 58° C. The lysed sample was then added to 120 μl of MagPrep Silica HS beads (diluted 1:2 in 50 mM 2-(N-morpholino)ethanesulfonic acid (MES) buffer), 200 μL binding buffer (7 M Guanidine HCl, 50 mM Tris HCl pH 7, 2% TWEEN® 20) and 200 μL ethanol (99.6%).

This mixture was then incubated with mixing every 5 minutes for 15 minutes and DNA was allowed to bind. The magnetic particles were separated from the mixture and washed twice, once in binding buffer and once in wash buffer (10 mM Tris HCl pH 6.5). The magnetic particles were then resuspended in 50 μL elution buffer (10 mM Tris HCl pH 8.6, 1 mM EDTA) and incubated for 15 minutes at 58° C., mixing every 5 minutes. DNA was eluted and separated from the magnetic particles.

The mixture depleted from the magnetic particles was added to 120 μl of MagPrep Silica beads (diluted 1:2 in 50 mM MES buffer) and RNA was allowed to bind. RNA bound particles were separated, washed twice in 800 μL wash buffer and RNA was eluted in 50 μl elution buffer (elution incubation was 7 minutes at 50° C. for RNA instead of 15 minutes).

Results

The DNA and RNA eluates were measured using a Qubit® 2.0 fluorometer (DNA and RNA BR assay kit) and spectral absorbances at 230, 260 and 280 nm were measured by a Nanodrop® 2000c. RNA integrity number (RIN) was assessed using an RNA 6000 Pico kit on an Agilent 2100 Bioanalyzer.

Generally, it is common for extracted nucleic acids to be contaminated with other molecules, such as proteins, organic compounds, etc. Nucleic acid purity can be determined by spectrophotometric analysis of the ratios or quotients of the absorbances at 260 nm/280 nm and at 260 nm/230 nm. It is generally accepted that pure DNA has a 260/280 ratio of 1.8 and a 260/230 ratio of 2, whereas pure RNA has a 260/280 ratio of 2 and a 260/230 ratio of 2.2

The results are presented in Table 1.

TABLE 1

| Sample | Qubit yield DNA (ng) | 260/280 DNA | 260/230 DNA | Qubit yield RNA (ng) | 260/280 RNA | 260/230 RNA | RIN |
|---|---|---|---|---|---|---|---|
| Brain FFPE sample 1 | 122 | 1.56 | 1.44 | 870 | 1.57 | 2.27 | 2.7 |
| Brain FFPE sample 2 | 159.5 | 1.53 | 1.40 | 880 | 1.58 | 2.18 | 2.5 |
| Brain FFPE average | 141 | 1.55 | 1.42 | 875 | 1.58 | 2.23 | 2.6 |

As can be seen in Table 1, the combination of xylene as organic phase and TWEEN® 20 as surfactant resulted in DNA and RNA yields with a reasonably high purity, i.e., few impurities, as assessed by the 260/280 and 260/230 ratios and acceptable high RIN values. When dealing with FFPE tissue, it is generally accepted that yields of >50 ng as assessed fluormetrically by Qubit are acceptable for providing sufficient input material in various downstream analyses. The expected RIN value for RNA from FFPE tissue is approximately 2. The RIN values in Table 1 are >2 indicating a higher than expected integrity of RNA extracted using the present invention.

Example 2

This example compares the deparaffinizing method disclosed in U.S. Pat. No. 8,574,868 with an embodiment of the present invention.
Sample Input Two slices (thickness 10 μm) of formalin-fixed, paraffin-embedded (FFPE) tissue sample from duplicate brain specimens were placed into a microcentrifuge tube for each deparaffinization method.
Deparaffinization A: U.S. Pat. No. 8,574,868

600 μl of 100% xylene was added into the microcentrifuge tube and mixed with the sample by vortexing for 10 seconds to form a mixture. The mixture was centrifuged to be at the bottom of the microcentrifuge tube. Then, 194 μl of RNase-free water was added into the microcentrifuge tube, and the microcentrifuge tube was placed in a temperature of 50° C. for shaking horizontally for 3 minutes. The microcentrifuge tube was centrifuged at 20,000×g for 3 minutes. Next, 550 μl of an upper layer liquid in the microcentrifuge tube was removed. After that, 600 μl of 100% xylene was added into the microcentrifuge tube again and mixed with the remaining liquid by vortexing for 10 seconds to form a mixture. The microcentrifuge tube was centrifuged at 20,000×g for 3 minutes. Finally, 600 μl of an upper layer liquid in the microcentrifuge tube was removed to leave a lower liquid containing deparaffinized tissue.
Deparaffinization B: Deparaffinization Method of the Invention 950 μl of 100% HISTOCHOICE® (Amresco) was added to the microcentrifuge tube and mixed with the sample by vortexing for 10 seconds. 50 μl of TWEEN® 20 was then added to the mixture and the sample was centrifuged for 2 minutes at 20,000×g. Next, 200 μl of MQ water was added to the tube, creating a third phase between the organic solvent and surfactant. 1 ml of liquid was then removed from the upper layers of liquid (organic phase and water) to leave a lower layer containing deparaffinized tissue.
Extraction 180 μl of a lysis buffer (100 mM NaCl, 500 mM Tris HCl pH 8.0, 1% SDS) was added to the sample, followed by 40 μl of Proteinase K (20 mg/ml) mixed and incubated for 40 minutes-2 hours at 58° C. The lysed sample was then added to 120 μl of MagPrep Silica HS beads (diluted 1:2 in 50 mM MES buffer), 200 μl binding buffer (7 M Guanidine HCl, 50 mM Tris HCl pH 7, 2% TWEEN® 20) and 200 μl ethanol (99.6%).

This mixture was then incubated with mixing every 5 minutes for 15 minutes and DNA allowed to bind. The magnetic particles were separated from the mixture and washed twice, once in binding buffer and once in wash buffer (10 mM TrisHCl pH 6.5). The magnetic particles were then resuspended in 50 μl elution buffer (10 mM Tris HCl pH 8.6, 1 mM EDTA) and incubated for 15 minutes at 58° C., mixing every 5 minutes. DNA was eluted and separated from the magnetic particles.

The mixture depleted from magnetic particles was added to 120 μl of MagPrep Silica beads (diluted 1:2 in 50 mM MES buffer) and RNA was allowed to bind. RNA bound particles were separated washed twice in 800 μl wash buffer and RNA was eluted in 50 μl elution buffer (elution incubation is 7 minutes at 58° C. for RNA instead of 15 minutes).
Results The DNA and RNA eluates were measured using a Qubit® 2.0 fluorometer (DNA and RNA BR assay kit) and spectral absorbances at 230, 260 and 280 nm were measured by a Nanodrop® 2000c. RNA integrity number (RIN) was assessed using an RNA 6000 Pico kit on an Agilent 2100 Bioanalyzer. The results are presented in Table 2.

TABLE 2

| Sample | Qubit yield DNA (ng) | 260/280 DNA | 260/230 DNA | Qubit yield RNA (ng) | 260/280 RNA | 260/230 RNA | RIN |
|---|---|---|---|---|---|---|---|
| Deparaffinization A (average) | 141 | 1.52 | 1.24 | 720 | 1.58 | 2.25 | 2.35 |
| Deparaffinization B (average) | 110 | 1.45 | 1.16 | 1108 | 1.62 | 1.99 | 2.65 |

Figure 10:
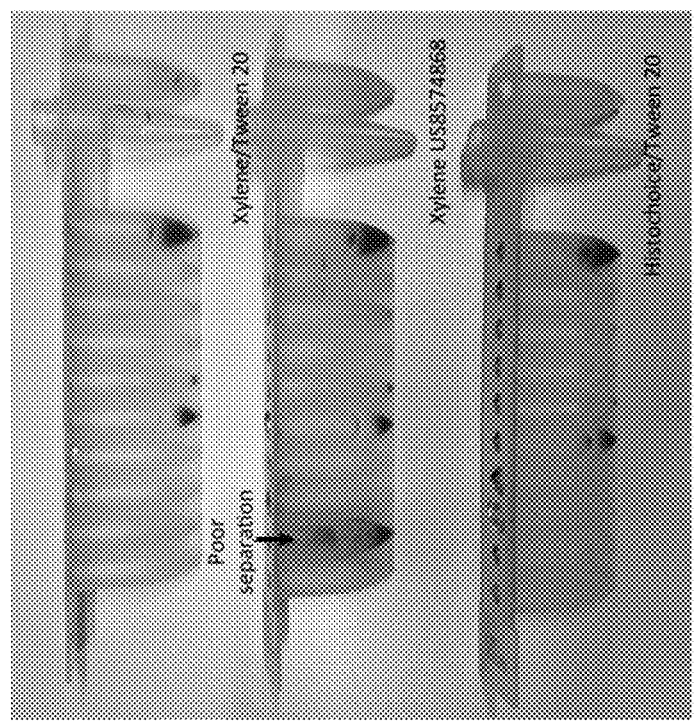
FIG. 10 illustrates a comparison of embodiments with prior art technology.

The total yield of nucleic acids and in particular the yield of RNA is higher with the deparaffinization method of the embodiments as compared to the deparaffinization method of U.S. Pat. No. 8,574,868. The deparaffinization method of the embodiments also resulted in higher RIN value, meaning that the RNA extracted had a higher integrity. In addition, deparaffinization A resulted in separation problems during the extraction process. In more detail and is further shown in FIG. 10 the magnetic beads failed to separate from the lysate. This is in clear contrast to the embodiments of the present invention according to Example 1 (Xylene/TWEEN® 20) and according to Example 2 (HISTOCHOICE®/TWEEN® 20).

Example 3

This example illustrates the removal of impurities by introducing a surfactant in the deparaffinization step. The deparaffinization method was performed with TWEEN® 20 as surfactant and with glycerol instead of the surfactant. Glycerol is a polyol ($C_3H_8O_3$) with a density of 1.261 g/ml, i.e., higher density as compared to water and HISTOCHOICE® as organic solvent. Accordingly, glycerol should form a lower phase during the phase separation and gather the deparaffinized tissue sample therein.

Deparaffinization

Three slices (thickness 10 μm) of formalin-fixed, paraffin-embedded (FFPE) tissue sample from duplicate spleen and liver specimens were placed into a microcentrifuge tube. Spleen specimens were embedded in polymer-free paraffin (Histowax, Histolab), and liver samples were embedded in a polymer-enriched paraffin (Paraplast, Leica Biosystems). 950 μl of 100% HISTOCHOICE® (Amresco) was added to the microcentrifuge tube and mixed with the sample by vortexing for 10 seconds. 50 μl of either glycerol or TWEEN® 20 was then added to the mixture and the sample was centrifuged for 2 minutes at 20,000×g. Next, 200 μl of MQ water was added to the tube. 1 ml of liquid was then removed from the upper layers of liquid (organic phase and water) to leave a lower layer containing deparaffinized tissue.

Extraction

180 μl of a lysis buffer (100 mM NaCl, 500 mM Tris HCl pH 8.0, 1% SDS) was added to the sample, followed by 40 μl of Proteinase K (20 mg/ml) mixed and incubated for 2 hours at 58° C. The lysed sample was then added to 120 μl of MagPrep Silica HS beads (diluted 1:2 in 50 mM MES buffer), 200 μl binding buffer (7 M Guanidine HCl, 50 mM Tris HCl pH 7, 2% TWEEN® 20) and 200 μl ethanol (99.6%).

This mixture was then incubated with mixing every 5 minutes for 15 minutes and DNA was allowed to bind. The magnetic particles were separated from the mixture and washed twice, once in binding buffer and once in wash buffer (10 mM Tris HCl pH 6.5). The magnetic particles were then resuspended in 50 μl elution buffer (10 mM Tris HCl pH 8.6, 1 mM EDTA) and incubated for 15 minutes at 58° C., mixing every 5 minutes. DNA was eluted and separated from the magnetic particles.

Results

The DNA eluates were measured using a Qubit® 2.0 fluorometer (DNA BR assay kit) and spectral absorbances at 230, 260 and 280 nm were measured by a Nanodrop® 2000c. The results are presented in Table 3.

TABLE 3

| Sample | Qubit yield DNA (ng) | 260/280 DNA | 260/230 DNA |
|---|---|---|---|
| Spleen/TWEEN® 20 | 6700 | 1.75 | 2.00 |
| Spleen/glycerol | 7500 | 1.70 | 1.75 |
| Liver/TWEEN® 20 | 1175 | 1.53 | 1.73 |
| Liver/glycerol | 820 | 1.24 | 1.48 |

This example illustrates that the surfactant not only serves the purpose of collecting the tissue, but it improves the purity of the samples, in particular the liver sample with polymer additives as illustrated by the 260/280 and 260/230 ratio in Table 3. Glycerol was also able to collect the tissue but failed to remove impurities as illustrated by lower 260/280 and 260/230 ratios.

Example 4

This example illustrates the usage of different organic solvents and surfactants in the deparaffinization method.

Organic Solvents

This example tested HISTOCHOICE® (Amresco), Clearene (Leica Biosystems) and xylene as organic solvents. HISTOCHOICE® with chemical name solvent naphta (petroleum), medium aliphatic is a non-polar solvent that is further defined in U.S. Pat. No. 5,344,637. Clearene is d-limonene, which is a cyclic terpene ($C_{10}H_{16}$), also referred to as 1-methyl-4-(1-methylethenyl)-cyclohexene. It is an unsaturated analogue of xylene and is non-polar. Xylene ($C_8H_{10}$), also referred to as xylol or dimethylbenzene, is a non-polar aromatic hydrocarbon containing a benzene ring with two methyl groups attached as substituents.

Surfactants

This example tested TWEEN® 20, diethanolamine, triethanolamine, Triton X-100 and IGEPAL® CA-630 as surfactants. Triton X-100, also referred to as polyethylene glycol p-(1,1,3,3-tetramethylbutyl)-phenyl ether, is a nonionic detergent with a density of 1.07 g/ml. The detergent is soluble in water in all proportions. IGEPAL® CA-630, also referred to as octylphenoxypolyethoxyethanol, is a nonionic detergent with a density of 1.07 g/ml.

Deparaffinization

950 μl of the organic solvent was added to 3×10 μm of paraplast heart FFPE tissue samples. The samples were mixed by vortexing for 10 seconds. 50 μl of surfactant was then added to the mixture and the sample was centrifuged for 2 minutes at 20,000×g. Next, 200 µl of MQ water was added and phase separation was observed. The samples were centrifuged at 20,000×g for 1 minute and phase separation was again observed. The results are presented in Table 4.

TABLE 4

| Organic solvent | Surfactant | Phase separation |
| --- | --- | --- |
| HISTOCHOICE ® | TWEEN ® 20 | 3 phases were formed |
| HISTOCHOICE ® | Diethanolamine | 3 phases were formed |
| HISTOCHOICE ® | Triton X-100 | No clear phase separation into 3 phases, aqueous phase appeared mixed with surfactant phase forming jelly-like substance |
| HISTOCHOICE ® | IGEPAL ® CA-630 | 3 phases were formed after $2^{nd}$ centrifugation |
| HISTOCHOICE ® | Triethanolamine | 3 phases were formed |
| Clearene | TWEEN ® 20 | 3 phases were formed, intermediate phase was milky |
| Clearene | Triton X-100 | No clear phase separation into 3 phases, aqueous phase appeared mixed with surfactant phase forming jelly-like substance |
| Xylene | TWEEN ® 20 | 3 phases were formed |

Of the tested combinations of organic solvent and surfactant, HISTOCHOICE® and TWEEN® 20 gave the best phase separation. Triton X-100 did not result in separation into three phases with any of the tested organic solvents. Triton X-100 is reported to be soluble in all proportions in water, whereas the other tested surfactants all had lower water solubility.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method for deparaffinizing a formalin-fixed paraffin-embedded (FFPE) tissue sample, said method comprising:
   mixing said FFPE tissue sample with an organic solvent to form a first mixture;
   adding a surfactant to said first mixture to form a second mixture;
   separating said second mixture into an organic solvent layer and a surfactant layer, wherein said surfactant layer comprises a deparaffinized tissue sample from said FFPE tissue sample; and
   adding water or an aqueous solution to said separated second mixture to form an organic solvent layer, a water or aqueous solution layer and a surfactant layer, wherein said surfactant layer comprises said deparaffinized tissue sample.

2. The method according to claim 1, wherein mixing said FFPE tissue sample with said organic solvent comprises:
   contacting said FFPE tissue sample with said organic solvent; and
   vortexing said FFPE tissue sample and said organic solvent to form said first mixture.

3. The method according to claim 1, wherein separating said second mixture comprises separating said second mixture into i) said organic solvent layer comprising paraffin from said FFPE tissue sample and ii) said surfactant layer comprising said deparaffinized tissue sample.

4. The method according to claim 1, wherein separating said second mixture comprises centrifuging said second mixture at a rotational speed and centrifugation time sufficient to separate said second mixture into said organic solvent layer and said surfactant layer and collecting said deparaffinized tissue sample in said surfactant layer.

5. The method according to claim 1, wherein separating said second mixture comprises incubating said second mixture in room temperature for a time period selected within an interval of from 5 minutes up to 60 minutes to allow said second mixture to settle into said organic solvent layer and said surfactant layer.

6. The method according to claim 1, wherein adding said water or aqueous solution to said separated second mixture comprises adding said water or aqueous solution to said separated second mixture to form an upper organic solvent layer, an intermediate water or aqueous solution layer and a bottom surfactant layer, wherein said bottom surfactant layer comprises said deparaffinized tissue sample.

7. The method according to claim 1, further comprising removing said organic solvent layer and said water or aqueous solution layer to retrieve said surfactant layer comprising said deparaffinized tissue sample.

8. The method according to claim 1, wherein said organic solvent has a density at room temperature within an interval of from 0.7 up to 0.9 g/ml; and
   said surfactant has a density at room temperature of at least 1.05 g/ml.

9. The method according to claim 8, wherein said organic solvent has a density at room temperature within an interval of from 0.725 up to 0.875 g/ml.

10. The method according to claim 9, wherein said organic solvent has a density at room temperature within an interval of from 0.75 up to 0.85 g/ml.

11. The method according to claim 8, wherein said surfactant has a density at room temperature of at least 1.1 g/ml.

12. The method according to claim 1, wherein said organic solvent is immiscible with said water or said aqueous solution.

13. The method according to claim 1, wherein said organic solvent is selected from a group consisting of xylene; toluene; a terpene; acids derived from unsubstituted or substituted cyclopentane, cyclopentene, cyclohexane or cyclohexene; unsubstituted or substituted saturated forms of fluorene, phenanthrene, anthracene, p-terphenyl fluoranthene, pyrene or chrysene; and unsubstituted or substituted saturated or partially-saturated quinoline, isoquinoline, pyridine, indole, acridine, carbazole, tetramethylene or pentamethylene sulfides.

14. The method according to claim 1, wherein said surfactant has a concentration selected so that said surfactant is not soluble in water or said aqueous solution.

15. The method according to claim 1, wherein said surfactant is a detergent.

16. The method according to claim 1, wherein said surfactant is selected from a group consisting of diethanolamine, triethanolamine, octylphenoxypolyethoxyethanol and polysorbates.

17. The method according to claim 16, wherein said surfactant is polysorbate 20.

18. The method according to claim 1, further comprising extracting nucleic acids from said deparaffinized tissue sample.

19. The method according to claim 18, wherein extracting said nucleic acids comprises:
   mixing said deparaffinized tissue sample with a lysis buffer to form a lysate;
   contacting said lysate with a solid phase that binds to said nucleic acids; and
   separating said solid phase from said lysate.

20. The method according to claim 19, wherein
   contacting said lysate comprises contacting said lysate with a first solid phase that selectively binds to a first species of nucleic acids; and
   separating said solid phase comprises separating said solid phase from said lysate to form a lysate depleted of said first species of nucleic acids, said method further comprising:
   contacting said lysate depleted of said first species of nucleic acids with a second solid phase that binds to a second species of nucleic acids; and
   separating said second solid phase from said lysate depleted of said first species of nucleic acids.

* * * * *